United States Patent
Gaur et al.

(10) Patent No.: US 10,774,023 B2
(45) Date of Patent: Sep. 15, 2020

(54) PROCESS AND CATALYSTS FOR THE PRODUCTION OF DIESEL AND GASOLINE ADDITIVES FROM GLYCEROL

(71) Applicant: Lyondell Chemical Technology, L.P., Houston, TX (US)

(72) Inventors: Sarthak Gaur, Houston, TX (US); Robert John Rebman, Pearland, TX (US); Daniel F. White, Houston, TX (US); Joseph P. Longtin, Pasadena, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 16/453,201

(22) Filed: Jun. 26, 2019

(65) Prior Publication Data

US 2020/0002257 A1    Jan. 2, 2020

Related U.S. Application Data

(60) Provisional application No. 62/692,203, filed on Jun. 29, 2018.

(51) Int. Cl.
| | |
|---|---|
| *C07C 41/09* | (2006.01) |
| *C07C 2/12* | (2006.01) |
| *C10L 1/185* | (2006.01) |
| *B01J 31/10* | (2006.01) |

(52) U.S. Cl.
CPC ............. *C07C 41/09* (2013.01); *B01J 31/10* (2013.01); *C07C 2/12* (2013.01); *C10L 1/1852* (2013.01); *C07C 2529/40* (2013.01); *C10L 2270/023* (2013.01)

(58) Field of Classification Search
CPC ....... C07C 41/09; C07C 2/12; C07C 2529/40; B01J 31/10; C10L 1/1852; C10L 2270/023; C10L 1/026; C10L 1/023
See application file for complete search history.

(56) References Cited

U.S. PATENT DOCUMENTS

| | | | | |
|---|---|---|---|---|
| 2008/0167503 A1* | 7/2008 | Yusof | ...................... | C07C 41/09 568/698 |
| 2009/0240086 A1* | 9/2009 | Barsa | ...................... | C07C 41/06 568/671 |
| 2010/0137668 A1* | 6/2010 | Loescher | .................. | C07C 2/28 585/504 |

FOREIGN PATENT DOCUMENTS

| | | | | |
|---|---|---|---|---|
| WO | WO-2007113776 A2 * | 10/2007 | ............. | C07C 41/09 |
| WO | WO-2008112910 A1 * | 9/2008 | ............. | C10L 1/026 |
| WO | 2013038029 A1 | 3/2013 | | |
| WO | WO201303029 A1 * | 3/2013 | ............. | C07C 41/00 |

OTHER PUBLICATIONS

Klepacova et al. ("tert-Butylation of glycerol catalyzed by ion-exchange resins", Applied Catalysis A: General 294, 2005, pp. 141-147).*
The International Search Report and the Written Opinion for PCT/US2019/039224 dated Oct. 4, 2019.
Aragón et al., Ind. Eng. Chem. Res., 1993, 32, pp. 2555-2562.
Aragón et al., Ind. Eng. Chem. Res., 1994, 33, pp. 592-599.
Zhao et al., Ind. Eng. Chem. Res. 2010, 49, pp. 12399-12404.

* cited by examiner

*Primary Examiner* — Rosalynd A Keys (57) ABSTRACT

A method of producing one or more glycerol ethers, the method comprising contacting glycerol and tertiary butanol (TBA) in the presence of an acidic catalyst to produce one or more glycerol ethers selected from mono-tert butyl glycerol ethers, di-tert butyl glycerol ethers, tri-tert butyl glycerol ethers, or a combination thereof; separating water and a stream comprising isobutylene, unreacted TBA, or a combination thereof from the one or more glycerol ethers; and recycling at least a portion of the stream comprising isobutylene, unreacted TBA, or a combination thereof to the contacting. Also disclosed is a process of co-producing isooctene, wherein the process involves contacting glycerol and tertiary butanol in the presence of a dehydrating catalyst and dimerizing/oligomerizing the dehydrated products in the presence of an oligomerizing catalyst to form isooctene, a precursor of isooctane and isomers thereof.

17 Claims, 2 Drawing Sheets

PROCESS AND CATALYSTS FOR THE PRODUCTION OF DIESEL AND GASOLINE ADDITIVES FROM GLYCEROL

CROSS-REFERENCE TO RELATED APPLICATIONS

This application claims the benefit of priority to U.S. Provisional Patent Application No. 62/692,203, filed on Jun. 29, 2018, which is incorporated herein by reference in its entirety.

TECHNICAL FIELD

This disclosure relates to the production of glycerol ethers and isooctane precursors. Still more specifically, this disclosure relates to the production of glycerol ethers and isooctene from tertiary butanol (TBA) and glycerol.

BACKGROUND

The combustion efficiency of internal combustion engines can be improved by the addition of oxygenated diesel fuel additives as well as the hydrocarbons that serve as the precursor to alkylate (isooctane) molecules, which are used as additives for gasoline. While the oxygenated ethers of glycerol are proposed to result in improved combustion efficiency, the alkylate molecules are known to improve the research octane number (RON) of gasoline. Accordingly, a need exists for improved systems and methods of producing glycerol ethers as well as alkylate precursors. Disclosed herein are embodiments directed to providing such systems and methods.

SUMMARY

Herein disclosed is a method of producing one or more glycerol ethers, the method comprising: contacting glycerol and tertiary butanol (hereafter referred to as TBA) in the presence of an acidic catalyst to produce one or more glycerol ethers selected from mono-tert butyl glycerol ethers, di-tert butyl glycerol ethers, tri-tert butyl glycerol ethers, or a combination thereof; separating water and a stream comprising isobutylene, unreacted TBA, or a combination thereof from the one or more glycerol ethers; and recycling at least a portion of the stream comprising isobutylene, unreacted TBA, or a combination thereof to the contacting.

Also disclosed herein is a system for producing one or more glycerol ethers, the system comprising: a reactive distillation column configured to contact glycerol and TBA in the presence of an acidic catalyst to produce an overhead comprising isobutylene, unreacted TBA, water, or a combination thereof and a bottoms comprising one or more glycerol ethers selected from mono-tert butyl glycerol ethers, di-tert butyl glycerol ethers, tri-tert butyl glycerol ethers, or a combination thereof; a separator configured to separate water from the overhead to provide a dewatered overhead comprising isobutylene, unreacted TBA, or a combination thereof; and a line configured to introduce at least a portion of the dewatered overhead to the reactive distillation column.

Also disclosed herein is a method comprising: introducing glycerol and TBA into a reactor comprising an acidic catalyst to produce one or more glycerol ethers selected from mono-tert butyl glycerol ethers, di-tert butyl glycerol ethers, tri-tert butyl glycerol ethers, or a combination thereof, wherein the reactor is operated at a molar ratio of TBA to glycerol in the range of from 2:1 to 7:1, from 2.5:1 to 7:1, or from 3:1 to 7:1.

Also disclosed herein is a method of producing at least one fuel additive, the method comprising: introducing glycerol and TBA into a reactor comprising an acidic catalyst effective to catalyze the reaction of glycerol and isobutylene to produce one or more glycerol ethers selected from mono-tert butyl glycerol ethers, di-tert butyl glycerol ethers, tri-tert butyl glycerol ethers, or combinations thereof, and an oligomerization catalyst effective to catalyze the oligomerization of isobutylene and thus provide one or more branched olefins including diisobutylene, wherein the contacting is performed at a molar ratio of TBA to glycerol in the range of from 2:1 to 7:1, from 2.5:1 to 7:1, or from 3:1 to 7:1; separating the isobutylene oligomers, isobutylene, or both from the one or more glycerol ethers; dimerizing and oligomerizing isobutylene to diisobutylene and isobutylene oligomers and hydrogenating at least a portion of the isobutylene oligomers to produce isooctane; and utilizing at least a portion of the one or more glycerol ethers as a diesel fuel additive, utilizing at least a portion of the isooctane as a gasoline fuel additive, or a combination thereof.

Also disclosed herein is a system for producing a fuel additive, the system comprising: a reactor comprising an acidic catalyst effective to catalyze the reaction of glycerol and TBA to produce one or more glycerol ethers selected from mono-tert butyl glycerol ethers, di-tert butyl glycerol ethers, tri-tert butyl glycerol ethers, or a combination thereof, and an oligomerization catalyst effective to catalyze the oligomerization of isobutylene to produce one or more branched olefins including diisobutylene; a separator configured to separate isobutylene, the isobutylene oligomers, or both from the one or more glycerol ethers; a hydrogenation reactor configured to hydrogenate at least a portion of the isobutylene oligomers to produce isooctane for use as a gasoline fuel additive; and a separator configured to separate one or more di-tert butyl ethers, tri-tert butyl ethers, or a combination thereof from the one or more glycerol ethers for use as a diesel fuel additive.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the detailed description hereinbelow is to be regarded as illustrative in nature and not restrictive.

BRIEF DESCRIPTION OF THE DRAWINGS

The following figures illustrate embodiments of the subject matter disclosed herein. The claimed subject matter may be understood by reference to the following description taken in conjunction with the accompanying figures, in which:

DETAILED DESCRIPTION

Overview

Herein disclosed are systems and methods for the synthesis of diesel additives comprising one or more glycerol ethers via contacting of glycerol and TBA in the presence of an acidic catalysts. The reaction products can comprise glycerol ethers, water and isobutylene. The glycerol ethers can include mono-tert butyl glycerol ethers (MBGE), di-tert butyl glycerol ethers (DTBE), tri-tert butyl glycerol ethers (TTBE), or a combination thereof. Without wishing to be limited by theory, a benefit of using TBA as a feedstock/alkylation agent in this reaction may be that TBA dehydrates to form isobutylene, in addition to providing the carbocation which may be the intermediate that alters the catalytic mechanism and results in the formation of glycerol ethers.

In embodiments, the method can further comprise separating water and a stream comprising isobutylene, unreacted TBA, or a combination thereof from the glycerol ethers. In embodiments, the method further comprises recycling at least a portion of the stream comprising isobutylene, unreacted TBA, or a combination thereof to the contacting of the glycerol and TBA in the presence of the acidic catalyst. A description of the method will now be made with reference to FIG. 1, which is a schematic of a system II for the production of glycerol ethers, according to an embodiment of this disclosure.

Figure 1:
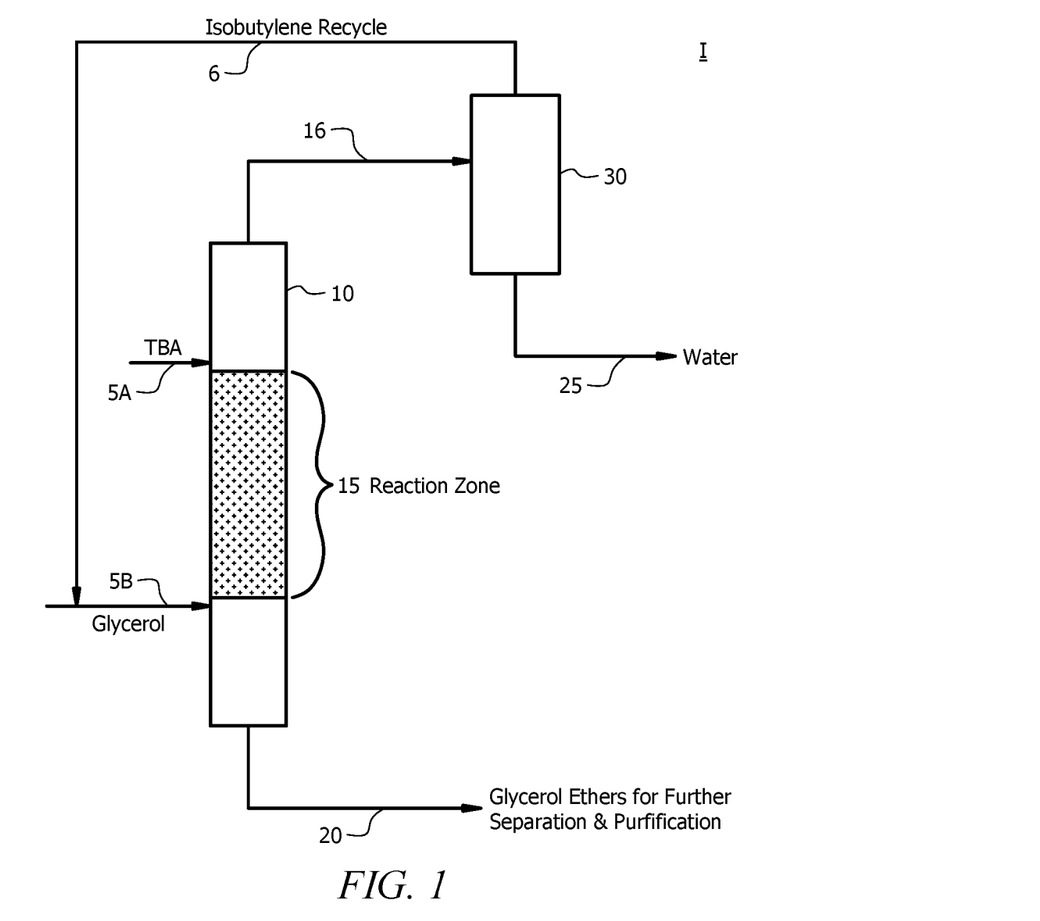
FIG. 1 is a schematic of a system I for the production of glycerol ethers, according to an embodiment of this disclosure.

System I comprises a reactor (also referred to as a tower or reactive distillation column or tower) 10, in which TBA and glycerol are converted to glycerol ethers, and a downstream separator 30, in which water is separated from an overhead of reactor 10. Although described with reference to a reactive distillation column, the contacting of the TBA and glycerol can be performed in a reactor. For example, reaction involving liquid acidic catalyst can be performed in a continuous stirred tank reactor (CSTR). Alternatively, in embodiments, acidic catalysts are utilized to catalyze the reaction in a fixed-bed reactor.

In embodiments, reactor 10 comprises a reactive distillation column or 'tower'. In embodiments, reactor 10 comprises a reactive distillation column configured to contact glycerol and TBA in the presence of an acidic catalyst (e.g., an acidic ion exchange catalyst) to produce an overhead stream 15 comprising isobutylene, unreacted TBA, water, or a combination thereof and a bottoms stream 20 comprising one or more glycerol ethers, including mono-tert butyl glycerol ethers, di-tert butyl glycerol ethers, tri-tert butyl glycerol ethers, or a combination thereof.

The reactive distillation column can comprise theoretical stages. In embodiments, reactor 10 comprises a reactive distillation column having from 20 to 60, from 30 to 50 or from 35 to 45 theoretical stages. In embodiments, TBA and glycerol are introduced into reactor 10 via TBA inlet line 5A and glycerol inlet line 5B, respectively. Reactor 10 contains therein an acidic catalyst effective to catalyze the production of glycerol ethers. Catalyst may be positioned within a reaction zone 15 of catalyst. In embodiments, a catalyst bed containing solid acidic catalyst can be placed between stages 20 to 40, between stages 25 to 35, or between stages 20 to 30, with the stages being counted from the bottom of the tower.

In embodiments, reaction zone 15 comprises an acidic catalyst. In embodiments, the acidic catalyst (e.g., within reaction zone 15) comprises a super acid catalyst. The super acid catalyst may comprise a Keggin structure, which is a structural form of heteropoly acids. By Keggin-type is indicated a structural form of α-Keggin anions, which have a general form of $[XM_{12}O_{40}]^{n-}$, where X is the heteroatom (such as $P^{+5}$, $Si^{+4}$, or $B^{+3}$), M is the addenda atom (such as molybdenum or tungsten), and O represents oxygen. The super acid catalyst (solid or liquid) can comprise, for example, Keggin-type polyoxometalates, such as tungstophosphoric acid, hypophosphoric acid, and AMBERLYST® 15. The super acid catalyst can have a Hammett acidity function $H_o$ in the range of from −12 to −16, in embodiments. These super acids can also be supported on an inert support, such as, without limitation, silica, alumina, zirconia, MCM-41. The super acids may be supported on the inert support by, for example, incipient wetness impregnation. Without wishing to be limited by theory, supporting the acidic catalyst may help the acidic catalysts maintain the Keggin structure, thereby helping to ensure the homogeneity of the acid sites of the supported acidic catalyst.

In embodiments, the acidic catalyst comprises an acidic ion exchange catalyst. In embodiments, the acidic ion exchange catalyst comprises sulfonic acid groups, is macroreticular, comprises a polymeric resin, is mesoporous (e.g., SBA-15 or MCM-41) or a combination thereof. As known to one of skill in the art, macroreticular refers to ion exchange catalysts comprising discrete pores, and mesoporous refers to having pores in the range of from 2 to 50 nm. In specific embodiments, suitable acidic ion exchange catalyst comprises AMBERLYST® 15Dry. In embodiments, suitable acidic ion exchange catalyst can be supported on silica (e.g., ordered mesoporous silica, such as SBA-15), alumina, zirconia, MCM-41, or a combination thereof.

In embodiments, the acidic catalyst is present in an amount in the range of from 1 to 10, from 2 to 6, or from 3 to 5 weight percent (wt %) of a reactant mixture comprising the TBA and the glycerol.

In embodiments, the feed reactants comprise crude and/or purified glycerol and TBA. As discussed further hereinbelow, hydrogen may be co-fed as a reactant. In embodiments, isobutylene is not fed as a reactant; isobutylene is produced in the reaction due to the dehydration of reactants. In embodiments, TBA may be co-fed with glycerol in molar excess, for example, with a molar ratio of glycerol to TBA in the range of from 1:2 to 1:7 (included). In embodiments, the molar ratio of TBA to glycerol introduced into reactor 10 is in the range of from 2:1 to 7:1, from 2.5:1 to 7:1, or from 3:1 to 7:1.

The feed (TBA, glycerol, recycled isobutylene, or a combination thereof) to the tower 10 can be introduced between stages 20 to 40, between stages 25 to 35, or between stages 20 to 30. In embodiments, the TBA and the glycerol are introduced to different locations along a vertical height (relative to a common point of reference such as ground level) of a reactive distillation column. In embodiments, the reactive distillation column 10 comprises an inlet whereby the TBA is introduced into the reactive distillation column via TBA inlet line 5A, an inlet whereby the glycerol is introduced into the reactive distillation column via glycerol inlet line 5B, and an inlet whereby the at least a portion of a dewatered overhead (described hereinbelow) from the separator 30 is introduced into the reactive distillation column 10. In embodiments, at least one of the inlets is disparate and located at a different vertical height from that of at least another of the inlets. For example, glycerol inlet line 5B may be configured to introduce glycerol and/or recycled isobutylene at or below the reaction zone 15, TBA inlet line 5A may be configured to introduce TBA at or above the reaction zone 15, or both. In embodiments, a recycle line from separator 30 to reactor 10 (e.g., line 6 discussed further hereinbelow) is fluidly connected with glycerol inlet line 5B, whereby recycled isobutylene is combined with the glycerol feed in glycerol inlet line 5B prior to introduction into the reaction section of tower 10.

Tower 10 may be configured to separate an overhead 15 comprising isobutylene, unreacted TBA, water, or a combination thereof from a bottoms 20 comprising glycerol ethers. The formation and presence of water during catalysis can result in a decrease in catalytic activity. To those aware of the art, water is known to suppress the acid sites of the catalyst, thereby shortening the life of the catalyst. Therefore, the removal of water may be critical to retaining the life and activity of the acidic catalyst. Thus, in embodiments, TBA and glycerol are fed in two separate sections of a reactive distillation column 10, resulting in the formation of MBGE, DTBE, and TTBE as well as unconverted glycerol as the bottoms stream and isobutylene, TBA and water as the overheads stream. The overheads stream is then introduced into a separator, such as a gas-liquid disengagement vessel, wherein water is removed and isobutylene is recovered and recirculated back to the reaction zone. The recycled isobutylene may be introduced along with or separately from the glycerol reactant, in embodiments. Thus, with reference to FIG. 1, in embodiments, overhead 15 is introduced into separator 30, wherein water 25 is removed therefrom, to provide a dewatered overhead stream 6 comprising isobutylene, unreacted TBA, or a combination thereof. Separating water from the overhead 15 to provide the dewatered overhead stream 6 comprising isobutylene, unreacted TBA, or a combination thereof can be performed in a separation apparatus or separator 30. For example, in embodiments, separator 30 can comprise a gas/liquid disengaging vessel.

In embodiments, at least a portion of the isobutylene in dewatered overhead stream in line 6 comprising isobutylene, unreacted TBA, or a combination thereof is recycled to reaction zone in tower 10. Thus, in embodiments, a line (e.g., line 6 or another recycle line comprising at least a portion of the dewatered overhead in line 6) is configured to introduce at least a portion of the dewatered overhead extracted from separator 30 via line 6 to the reactive distillation column 10. In embodiments, an amount of isobutylene in the at least a portion of the stream comprising isobutylene, unreacted TBA, or a combination thereof recycled to the contacting via dewatered overhead stream 6 is present such that a molar ratio of isobutylene to glycerol fed to reactor 10 is in the range of 2:1 to 6:1, from 2:1 to 4:1, or less than or equal to 6:1. The recycling of isobutylene that is produced in the reaction to the reaction zone can provide for an increased yield and selectivity to the desired products (e.g., DTBE, TTBE).

The isobutylene that is produced during the contacting of the TBA and glycerol can be oligomerized into branched olefins, such as 2,4,4-trimethyl-2-pentene and 2,4,4-trimethyl-1-pentene, which can be readily hydrogenated to form isooctane, which is utilizable as a gasoline additive. In embodiments according to this disclosure, such oligomerization is performed in situ, potentially making the herein-disclosed process more economically attractive by providing a diesel additive (e.g., DTBE and/or TTBE) and a gasoline additive or gasoline additive precursor (e.g., branched olefins from which isooctane can be produced) in a single step. Thus, according to embodiments of this disclosure, diesel additives (oxygenates comprising glycerol ethers) and precursors for gasoline additives (branched olefins) can be formed in a single step. In embodiments, the reaction products of the conversion of TBA and glycerol via reaction in the presence of an acidic catalyst are converted to branched olefins via contact with an oligomerization catalyst within the reactor.

Figure 2:
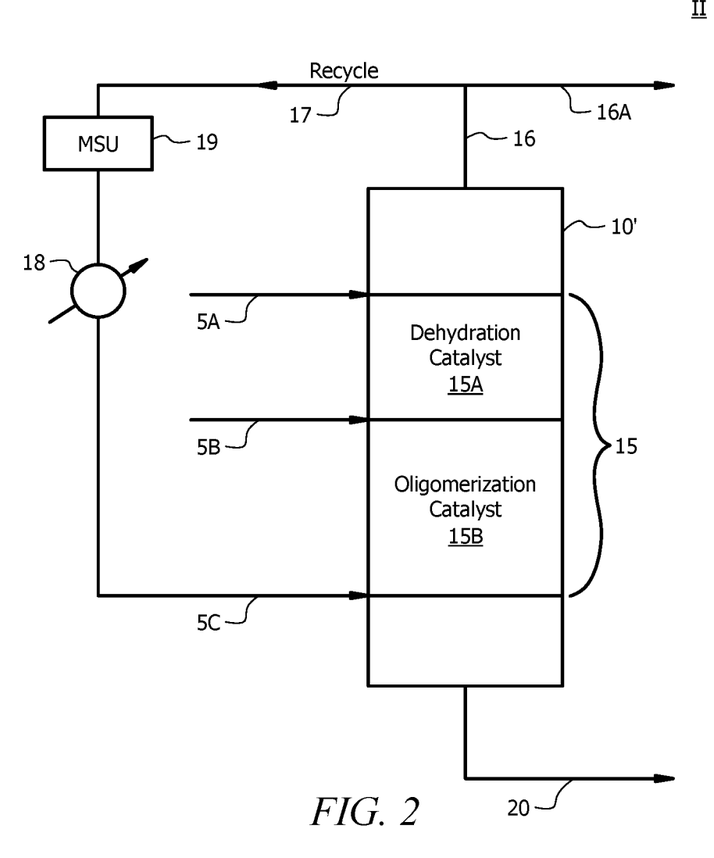
FIG. 2 is a schematic of a system II for the production of glycerol ethers and isooctane according to another embodiment of this disclosure.

A system further comprising an oligomerization catalyst will now be described with reference to FIG. 2, which is a schematic of a system II for the production of glycerol ethers according to another embodiment of this disclosure. In the embodiment of FIG. 2, reactor 10' comprises a first catalyst in a first reaction zone 15A and a second catalyst in a second reaction zone 15B. In embodiments an acidic catalyst (also referred to herein as an acidic dehydration catalyst or more simply, a dehydration catalyst) as described hereinabove with reference to the embodiment of FIG. 1, is positioned in first reaction zone 15A. Reactor 10' further contains an oligomerization catalyst in second reaction zone 15B. The oligomerization catalyst is effective to catalyze the oligomerization of isobutylene to produce one or more branched olefins. Such branched olefins include, without limitation, 2,4,4-trimethyl-2-pentene, 2,4,4-trimethyl-1-pentene, or a combination thereof. In embodiments, reactor 10' thus can comprise a reaction zone 15 of the reactor comprising a first reaction zone 15A containing an acidic dehydration catalyst such as, without limitation, AMBERLYST® 15Dry, and a second reaction zone 15B containing an oligomerization catalyst, such as, without limitation, HZSM-5. Any efficacious oligomerization catalyst can be employed. In embodiments, the oligomerization catalyst comprises a medium pore zeolite having a structure comprising ten tetrahedra in a ring.

In embodiments, such as that of FIG. 2, reactor 10' can comprise a reactive distillation column, having positioned therein an acidic dehydration catalyst and an oligomerization catalyst. By way of example, in such embodiments, the acidic dehydration catalyst (e.g., within first reaction zone 15A) can be located between stages 30 to 40 of the extractive distillation column and the oligomerization catalyst (e.g., within second reaction zone 15B) can be positioned between stages 20 to 30 of the reactive distillation column, with the stages in the reactive distillation column being counted from a bottom to a top thereof. Such an arrangement of the two catalysts may facilitate the dehydration of TBA over the acidic dehydration catalyst to form dehydration products and the subsequent oligomerization of the dehydration products to form branched olefins and glycerol ethers.

In some embodiments comprising an oligomerization catalyst zone, the acidic catalyst and the oligomerization catalyst can comprise an amount in the range of from 1 to 10, from 2 to 6, or from 3 to 5 weight percent (wt %) of a reactant mixture comprising the TBA and the glycerol.

As noted above, a process according to this disclosure may utilize a stand-alone CSTR. For example, a process of this disclosure may employ an acidic ion exchange catalyst (e.g., AMBERLYST® 15) and an oligomerization catalyst (e.g., medium pore HZSM5-type zeolite) in a stirred tank reactor.

The process occurs over a wide range of temperature and pressure. Within the reaction zone of reactor 10/10', the contacting can be performed at a temperature in the range of from room temperature to 240° C., from 100° C. to 220° C., from 150° C. to 200° C.; a pressure in the range of from atmospheric pressure to 500 psig, from 30 psig to 500 psig, from 100 psig to 500 psig, or greater than or equal to 30, 50, 75, 100, 150, 160, 170, 180, 190, 200, 300, 400, or 500 psig; or a combination thereof. In embodiments, the contacting is performed at a temperature in the range of from room temperature to 100° C., from 60° C. to 80° C., or greater than or equal to 30° C., 40° C., or 50° C.; a pressure in the range of from atmospheric pressure to 40 psig, from 10 psig to 30 psig, from 15 psig to 25 psig, or greater than or equal to 10, 15, or 20 psig; or a combination thereof. In embodiments, the dimerization and oligomerization of isobutylene over the oligomerization catalyst (e.g., HZSM-5) is performed at high temperature (e.g., greater than or equal to 200° C.) and high pressure (e.g., greater than or equal to 200 psig of hydrogen, where hydrogen is charged in the reactor along with reactants). High temperature in this case denotes a suitable temperature that is required for the activation of isobutylene on the surface of the oligomerization catalyst to form oligomerization products. High pressure in this case denotes the autogenous pressure resulting from high reactor temperature. Without wishing to be limited by theory, operation at high temperature and pressure may take advantage of the endothermicity of the reaction and drive the reaction to completion but also towards the formation of thermodynamically favored products.

In embodiments, the process involves recycling at least a portion of the overhead stream 16 from tower 10' via recycle line 17, preheating the stream using a side reboiler 18, and feeding the recycled stream below the bottom of the oligomerization catalyst, as shown by stream 5C in FIG. 2. The recycle stream 17 can constitute between 30-80% of the overhead stream 16, between 40-70% of the overhead stream 16; or between 50-60% of the overhead stream. The remainder of overhead stream 16 may be extracted via non-recycle line 16A.

In other embodiments, water from recycle stream 17 can be removed by utilizing a suitable water removal media such as a molecular sieve unit (MSU), as shown by block 19 in FIG. 2.

In embodiments, the contacting in the reaction zone (e.g., 10/10' is performed in the further presence of hydrogen. For example, hydrogen may be utilized to pressurize the reactor (e.g., reactor 10/10'), in embodiments. The reaction within reaction zone 15 can thus be performed in the presence of hydrogen pressurization to provide a pressure above atmospheric pressure (such operating pressures noted hereinabove); such pressurization may result in hydrocracking of the reactants. In such embodiments, hydrogen may be introduced via line 5C; or, via line 5B.

In embodiments, DTBE and TTBE may be desired products. In embodiments, therefore, di-tert butyl glycerol ethers, tri-tert butyl glycerol ethers, or a combination thereof can be separated from the reaction product comprising the glycerol ethers (e.g., in bottoms stream 20). In such embodiments, the system can further comprise a separator configured to separate di-tert butyl glycerol ethers, tri-tert butyl glycerol ethers, or a combination thereof from the product comprising the glycerol ethers. The DTBE and/or TTBE can be utilized as a diesel fuel additive. For example, in embodiments, the DTBE and TTBE can be combined and blended with diesel fuel, optionally subsequent further purification and/or separation steps.

In embodiments employing an oligomerization catalyst (such as the embodiment depicted in FIG. 2), the method can further comprise separating branched olefins from the glycerol ether product (e.g., from the glycerol ether product in bottoms 20). The branched olefins may be utilizable as a gasoline fuel additive or a precursor therefor. In embodiments, at least a portion of the branched olefins is hydrogenated to provide isooctane, which may be utilizable as a gasoline fuel additive. In such embodiments, a system of this disclosure (e.g., system I/II/) can further comprise a hydrogenation vessel into which hydrogen and branched olefins are introduced, and from which isooctane is removed. The separator for separating branched olefins from the glycerol ether product may be the same or a different separator (e.g., may be upstream or downstream) from a separator for separating the di-tert butyl glycerol ethers, tri-tert butyl glycerol ethers, or the combination thereof from the reaction product comprising the glycerol ethers.

In embodiments, the herein disclosed system and method for the production of glycerol ethers provide for an overall selectivity to glycerol ethers (defined as carbon selectivity) of at least 15, 16, 17, 18, 19, or 20 percent (%). In embodiments, the selectivity to DTBE and TTBE can be in the range of from 15 to 40% or from 20 to 40%, or greater than or equal to 15, 16, 17, 18, 19, or 20%. In embodiments, the herein disclosed system and method for the production of glycerol ethers provide for a glycerol conversion (defined as the moles of glycerol converted divided by the moles of glycerol fed) is at least 70, 75, or 80%. In embodiments, the herein disclosed system and method for the production of glycerol ethers provide for a TBA conversion (defined as the moles of TBA converted divided by the moles of TBA fed) of at least 55, 60, or 65%. In embodiments, the herein disclosed system and method for the production of glycerol ethers provides for an overall olefin selectivity (defined as selectivity towards C2-C12 olefins on a carbon basis) of at least 40, 60, or 85%. In embodiments, the herein disclosed system and method for the production of glycerol ethers provides for a selectivity to diisobutylene (defined as selectivity towards diisobutylene on a carbon basis) of at least 35, 40, or 45 wt %. The DIB may comprise a liquid mixture containing the two octylenes 2,4,4-trimethyl-1-pentene and 2,4,4-trimethyl-2-pentene.

Features

According to this disclosure, TBA can be utilized to produce diesel fuel additive(s). In this manner, TBA produced, for example, in a propylene oxide/tertiary butyl alcohol (PO/TBA) plant can be utilized to produce additives for diesel fuel, which may be utilized, for example, in heavy hauling applications.

Biodiesel is becoming increasingly popular, with one pound of glycerol being produced as a by-product for every ten pounds of biodiesel produced. According to this disclosure, such glycerol may be utilized to produce diesel additives that may be blended with (e.g., the product) biodiesel.

Via tandem utilization of an acidic dehydration catalyst and an oligomerization catalyst, as described herein, diesel additive(s) and gasoline additive(s) and/or precursor(s) for gasoline additive(s) can be produced. In embodiments, the diesel additive(s) and gasoline additive(s) and/or precursor(s) for gasoline additive(s) can be produced in a single step or reactor. This may be advantageous for refining facilities that co-produce gasoline and diesel.

The following examples merely illustrate the system and method of this disclosure. Those skilled in the art will recognize many variations that are within the spirit of this disclosure and the scope of the claims.

EXAMPLES

Example 1: Production of Glycerol Ethers at Low Pressure and Via CSTR

Glycerol ethers were produced in a reaction conducted at ambient pressure and 70° C. in a Parr CSTR. Table 1 below shows the results of the laboratory run with TBA:glycerol molar ratios of 4:1, 5:1, and 6:1.

TABLE 1

Results from Example 1

| TBA: Glycerol Ratio (Molar) | Glycerol Conversion (%) | MBGE Selectivity | DTBE Selectivity | TTBE Selectivity |
| --- | --- | --- | --- | --- |
| 4:1 | 70% | 70% | 30% | None |

Example 2: Production of Glycerol Ethers at Elevated Pressure and with Hydrogen Pressurization An experiment was conducted in which glycerol and TBA were mixed in a molar ratio of 4:1 and the mixture was charged in a 50 cc Autoclave reactor fitted with an impeller. In addition, AMBERLYST® 15Dry catalyst representing 9.32 wt % of the reactant mixture was charged in the reactor. The mixture was stirred with the impeller set to 750 rpm and heated to 110° C., which resulted in an increase in pressure in the reactor due to the formation of gaseous products and reactants. The mixture was then charged with hydrogen to a pressure of 500 psig. The pressure of the reactor increased to a final pressure of 600 psig due to the enthalpy changes associated with the latent heat of vaporization of liquid reactants to gaseous vapors. Subsequently, the mixture was stirred for 5 hours. After five hours, the reactor was cooled below 20° C. in an ice bath. Following this, the liquid contents of the reactor were transferred to a one-ounce glass vial for storage and further analysis. The sample vial was then weighed to calculate the amount of liquid product. The gaseous contents were analyzed in a gas bag and analytical results reconciled for the purposes of mass balance. The contents were analyzed on an Agilent 6890 gas chromatograph (GC) equipped with a DB-624 column.

The results from the experiment of this Example 2 are shown in Table 2 below. The results indicate that under the presence of hydrogen, the overall selectivity towards (mono-, di-, and tri-ethers) is around 19%.

TABLE 2

| Results from Example 2 | |
|---|---|
| Glycerol Conversion (%) | 83.65 |
| TBA Conversion (%) | 68.21 |
| Olefin Selectivity (Overall, %) | 43.01 |
| Isobutylene Selectivity (%) | 37.69 |
| DIB Selectivity (%) | 5.32 |
| Oxygenate Selectivity (Overall, %) | 1.67 |
| C2 (%) | 0.01 |
| C3 (%) | 0.43 |
| C4 (%) | 0.05 |
| C5 (%) | 0.00 |
| C6 (%) | 0.02 |
| C7 (%) | 0.05 |
| C8 (%) | 1.11 |
| Aromatics Selectivity (%) | 0.00 |
| Acids Selectivity (Overall, %) | 0.00 |
| Paraffin Selectivity (%) | 0.16 |
| Glycerol Ethers Selectivity (Overall, %) | 18.92 |

Example 3: Production of Glycerol Ethers at Elevated Pressure and Utilizing Oligomerization Catalyst Along with Acidic Dehydration Catalyst An experiment was conducted in which glycerol and TBA were mixed in a molar ratio of 4:1 and the mixture was charged in a 50 cc Autoclave reactor fitted with an impeller. In addition, an equal amount of AMBERLYST® 15Dry catalyst and HZSM5 zeolite, together representing 9.32 wt % of the reactant mixture was charged in the reactor. The mixture was first stirred with the impeller set to 750 rpm and heated at 70° C. under 5 psig of hydrogen pressure for 6 hours. The pressure of the reactor increased to a final pressure of 30 psig due to the enthalpy changes associated with the latent heat of vaporization of liquid reactants to gaseous vapors. After this step, reactor was pressurized with 200 psig hydrogen and contents of the reactor were subsequently heated to 210° C. while pressurized under 200 psig of hydrogen. The pressure of the reactor increased to a final pressure of 500 psig due to the latent heat of vaporization of liquid reactants. As mentioned earlier, hydrogen was introduced to accelerate the hydrocracking of the reactants. Subsequently, the mixture was reacted for 25 hours at 500 psi. After 25 hours, the reactor was cooled below 20° C. in an ice bath. Following this, the liquid contents of the reactor were transferred to a one-ounce glass vial for storage and further analysis. The sample vial was then weighed to calculate the amount of liquid product. The gaseous contents were analyzed in a gas bag and analytical results reconciled for the purposes of mass balance. Results from the experiment of this Example 3 are shown in the Table 3 below.

TABLE 3

| Results from Example 3 | |
|---|---|
| Glycerol Conversion (%) | 62.45 |
| TBA Conversion (%) | 75.07 |
| Olefin Selectivity (Overall, %) | 88.09 |
| C4 (%) | 33.48 |
| C7 (%) | 1.62 |
| C8 (%) | 47.30 |
| C9 (%) | 3.05 |
| C12 (%) | 2.64 |
| Oxygenate Selectivity (Overall, %) | 8.18 |
| C2 (%) | 1.09 |
| C3 (%) | 4.92 |
| C4 (%) | 1.95 |
| C5 (%) | 0.02 |
| C6 (%) | 0.00 |
| C7 (%) | 0.00 |
| C8 (%) | 0.22 |
| Aromatics Selectivity (%) | 0.87 |
| Acids Selectivity (Overall, %) | 0.67 |
| Paraffin Selectivity (%) | 0.00 |
| Glycerol Ethers Selectivity (Overall, %) | 2.19 |

The results in Table 3 indicate that at high temperature, the selectivity to acyclic branched olefins increased to 88%. These olefinic components comprised hydrocarbons in the C4 to C12 range, a majority of which was constituted by diisobutylene (C8), which can be further hydrogenated to produce isooctane. Isooctane may be utilized as a gasoline additive to improve the Research Octane Number (RON). The presence of hydrogen in the reactor appears to shift the selectivity towards the formation of olefinic components. On the other hand, the selectivity towards the formation of oxygenates and glycerol ethers decreased due to the oligomerization of isobutylene which is formed in the reaction. To increase the selectivity to branched acyclic olefins, the TBA to glycerol molar ratio may be greater than 3:1. As noted above, without wishing to be limited by theory, TBA is hypothesized to provide the carbo-cation which is responsible for the pathway leading to the formation of C8 hydrocarbons, such as DIB.

Additional Disclosure

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A method of producing one or more glycerol ethers, the method comprising: contacting glycerol and tertiary butanol (TBA) in the presence of an acidic catalyst to produce one or more glycerol ethers selected from mono-tert butyl glycerol ethers, di-tert butyl glycerol ethers, tri-tert butyl glycerol ethers, or a combination thereof; separating water and a stream comprising isobutylene, unreacted TBA, or a combination thereof from the one or more glycerol ethers; and recycling at least a portion of the stream comprising isobutylene, unreacted TBA, or a combination thereof to the contacting.

B: A system for producing one or more glycerol ethers, the system comprising: a reactive distillation column configured to contact glycerol and tertiary butanol (TBA) in the presence of an acidic catalyst to produce an overhead comprising isobutylene, unreacted TBA, water, or a combination thereof and a bottoms comprising one or more glycerol ethers selected from mono-tert butyl glycerol ethers, di-tert butyl glycerol ethers, tri-tert butyl glycerol ethers, or a combination thereof; a separator configured to separate water from the overhead to provide a dewatered overhead comprising isobutylene, unreacted TBA, or a combination thereof; and a line configured to introduce at least a portion of the dewatered overhead to the reactive distillation column.

C: A method comprising: introducing glycerol and tertiary butanol (TBA) into a reactor comprising an acidic catalyst to produce one or more glycerol ethers selected from mono-tert butyl glycerol ethers, di-tert butyl glycerol ethers, tri-tert butyl glycerol ethers, or a combination thereof, wherein the reactor is operated at a molar ratio of TBA to glycerol in the range of from 2:1 to 7:1, from 2.5:1 to 7:1, or from 3:1 to 7:1.

D: A method of producing at least one fuel additive, the method comprising: introducing glycerol and tertiary butanol (TBA) into a reactor comprising an acidic catalyst effective to catalyze the reaction of glycerol and isobutylene to produce one or more glycerol ethers selected from mono-tert butyl glycerol ethers, di-tert butyl glycerol ethers, tri-tert butyl glycerol ethers, or combinations thereof, and an oligomerization catalyst effective to catalyze the oligomerization of isobutylene and thus provide one or more branched olefins including diisobutylene, wherein the contacting is performed at a molar ratio of TBA to glycerol in the range of from 2:1 to 7:1, from 2.5:1 to 7:1, or from 3:1 to 7:1; separating the isobutylene oligomers, isobutylene, or both from the one or more glycerol ethers; hydrogenating at least a portion of the isobutylene oligomers to produce isooctane; and utilizing at least a portion of the one or more glycerol ethers as a diesel fuel additive, utilizing at least a portion of the isooctane as a gasoline fuel additive, or a combination thereof.

E: A system for producing a fuel additive, the system comprising: a reactor comprising an acidic catalyst effective to catalyze the reaction of glycerol and tertiary butanol (TBA) to produce one or more glycerol ethers selected from mono-tert butyl glycerol ethers, di-tert butyl glycerol ethers, tri-tert butyl glycerol ethers, or a combination thereof, and an oligomerization catalyst effective to catalyze the oligomerization of isobutylene to produce one or more branched olefins including diisobutylene; a separator configured to separate isobutylene, the isobutylene oligomers, or both from the one or more glycerol ethers; a hydrogenation reactor configured to hydrogenate at least a portion of the isobutylene oligomers to produce isooctane for use as a gasoline fuel additive; and a separator configured to separate one or more di-tert butyl ethers, tri-tert butyl ethers, or a combination thereof from the one or more glycerol ethers for use as a diesel fuel additive.

Each of embodiments A, B, C, D, and E may have one or more of the following additional elements:

Element 1: wherein the molar ratio of TBA to glycerol is in the range of from 2:1 to 7:1, from 2.5:1 to 7:1, or from 3:1 to 7:1. Element 2: wherein the separating comprises separating an overhead comprising isobutylene, unreacted TBA, water, or a combination thereof from a bottoms comprising the one or more glycerol ethers, and separating water from the overhead to provide the stream comprising isobutylene, unreacted TBA, or a combination thereof. Element 3: wherein an amount of isobutylene in the at least a portion of the stream comprising isobutylene, unreacted TBA, or a combination thereof recycled to the contacting is present such that a molar ratio of isobutylene to glycerol is in the range of 2:1 to 6:1, from 2:1 to 4:1, or less than or equal to 6:1. Element 4: wherein the separating of the water from the overhead to provide the stream comprising isobutylene, unreacted TBA, or a combination thereof is performed in a gas/liquid disengaging vessel. Element 5: wherein the contacting is performed in a reactive distillation column. Element 6: wherein the TBA and the glycerol are introduced to different locations along a vertical height of the reactive distillation column. Element 7: further comprising separating di-tert butyl glycerol ethers, tri-tert butyl glycerol ethers, or a combination thereof from the one or more glycerol ethers. Element 8: wherein the contacting is performed at a temperature in the range of from room temperature to 100° C., from 60° C. to 80° C., or greater than or equal to 30° C., 40° C., or 50° C.; a pressure in the range of from atmospheric pressure to 40 psig, from 10 psig to 30 psig, from 15 psig to 25 psig, or greater than or equal to 10, 15, or 20 psig; or a combination thereof. Element 9: wherein the reactive distillation column comprises an inlet whereby the TBA is introduced into the reactive distillation column, an inlet whereby the glycerol is introduced into the reactive distillation column, and an inlet whereby the at least a portion of the dewatered overhead from the separator is introduced into the reactive distillation column, and wherein at least one of the inlets is disparate and located at a different vertical height from that of at least another of the inlets. Element 10: wherein the separator comprises a gas/liquid disengaging vessel. Element 11: wherein the acidic catalyst has a Hammett acidity function $H_o$ in the range of from −12 to −16. Element 12: wherein the acidic catalyst comprises an acidic ion exchange catalyst, and wherein the acidic ion exchange catalyst comprises sulfonic acid groups, is macroreticular, comprises a polymeric resin, or a combination thereof. Element 13: wherein the acidic catalyst is selected from AMBERLYST®15Dry, or a keggin-type polyoxometalate supported on silica/alumina/zirconia/MCM-41/SBA-15 or a combination thereof. Element 14: further comprising a separator configured to separate di-tert butyl glycerol ethers, tri-tert butyl glycerol ethers, or a combination thereof from the one or more glycerol ethers for use as a diesel fuel additive. Element 15: further comprising separating water and a stream comprising isobutylene, unreacted TBA, or a combination thereof from the one or more glycerol ethers. Element 16: further comprising recycling at least a portion of the stream comprising isobutylene, unreacted TBA, or a combination thereof to the contacting. Element 17: wherein the acidic catalyst has a Hammett acidity function $H_o$ in the range of from −12 to −16. Element 18: wherein the acidic catalyst comprises an acidic ion exchange catalyst. Element 19: wherein the reactor further contains an oligomerization catalyst effective to catalyze the oligomerization of isobutylene and thus provide one or more branched olefins. Element 20: wherein a reaction zone of the reactor contains an acidic catalyst comprising a dehydration catalyst such as AMBERLYST® 15Dry as well as an oligomerization catalyst such as HZSM-5 in tandem. Element 21: wherein the reactor comprises a reactive distillation column, and wherein the dehydration catalyst is positioned in the reactive distillation column between stages 30-40 and the oligomerization catalyst is positioned in the reactive distillation column between stages 20-30, whereby the dehydration of TBA over the dehydration catalyst to form dehydration products and subsequent oligomerization of the dehydration products to form branched olefins and glycerol ethers are facilitated, and wherein the stages in the reactive distillation column are counted from a top to a bottom thereof. Element 22: further comprising recycling a portion of the overhead stream from the reactive distillation column, removing water by using a molecular sieve zeolite bed, and feeding the recycled (and dewatered) stream to the bottom of the oligomerization catalyst; or below stage 20 in a reactive distillation tower. Element 23: further comprising separating one or more of the one or more branched olefins from the one or more glycerol ethers for use as a gasoline fuel additive or a precursor therefor. Element 24: wherein the one or more branched olefins comprise 2,4,4-trimethyl-2-pentene, 2,4,4-trimethyl-1-pentene, or a combination thereof. Element 25: further comprising hydrogenating the one or more branched olefins to provide isooctane for use as a gasoline fuel additive. Element 26: wherein the contacting is performed at a temperature in the range of from room temperature to 240° C., from 100° C. to 220° C., from 150° C. to 200° C.; a pressure in the range of from atmospheric pressure to 500 psig, from 30 psig to 500 psig, from 100 psig to 500 psig, or greater than or equal to 30, 50, 75, 100, 150, 160, 170, 180, 190, 200, 300, 400, or 500 psig; or a combination thereof. Element 27: wherein an overall selectivity to glycerol ethers (defined as carbon selectivity) is at least 15, 16, 17, or 18 percent (%), wherein a glycerol conversion (defined as the moles of glycerol converted divided by the moles of glycerol fed) is at least 70, 75, or 80 wt %, wherein a TBA conversion (defined as the moles of TBA converted divided by the moles of TBA fed) is at least 55, 60, or 65 wt %, or a combination thereof. Element 28: wherein the contacting is performed in the presence of hydrogen. Element 29: wherein the acidic catalyst is present in an amount in the range of from 1 to 10, from 2 to 6, or from 3 to 5 weight percent (wt %) of a reactant mixture comprising the TBA and the glycerol. Element 30: wherein the oligomerization catalyst comprises a medium pore zeolite having a structure comprising ten tetrahedra in a ring. Element 31: wherein an overall selectivity to glycerol ethers (defined as carbon selectivity) is at least 15, 16, 17, or 18 percent (%), wherein a glycerol conversion (defined as the moles of glycerol converted divided by the moles of glycerol fed) is at least 70, 75, or 80 wt %, wherein a TBA conversion (defined as the moles of TBA converted divided by the moles of TBA fed) is at least 55, 60, or 65%, wherein an overall olefin selectivity (defined as selectivity towards C2-C12 olefins on a carbon basis) is at least 40, 60, or 85%, or a combination thereof. Element 32: wherein a selectivity to diisobutylene (defined as selectivity towards diisobutylene on a carbon basis) is at least 35, 40, or 45 wt %. Element 33: wherein the reaction is performed in the presence of hydrogen pressurization to provide a pressure above atmospheric pressure and enhance hydrocracking of the reactants. Element 34: wherein the acidic catalyst and the oligomerization catalyst comprise an amount in the range of from 1 to 10, from 2 to 6, or from 3 to 5 weight percent (wt %) of a reactant mixture comprising the TBA and the glycerol. Element 35: wherein the separator configured to separate isobutylene, the isobutylene oligomers/branched olefins, or both from the one or more glycerol ethers and the separator configured to separate one or more di-tert butyl ethers, tri-tert butyl ethers, or a combination thereof from the one or more glycerol ethers for use as a diesel fuel additive comprise the same separator, the reactor, or a combination thereof. Element 36: further comprising a line for introducing at least a portion of the isobutylene from the separator configured to separate isobutylene, the isobutylene oligomers, or both from the one or more glycerol ethers to the reactor, optionally subsequent the removal of any water therein via a de-watering apparatus.

While certain embodiments have been shown and described, modifications thereof can be made by one skilled in the art without departing from the teachings of this disclosure.

Numerous other modifications, equivalents, and alternatives, will become apparent to those skilled in the art once the above disclosure is fully appreciated. It is intended that the following claims be interpreted to embrace such modifications, equivalents, and alternatives where applicable. Accordingly, the scope of protection is not limited by the description set out above but is only limited by the claims which follow, that scope including equivalents of the subject matter of the claims.

What is claimed is:
1. A method of producing one or more glycerol ethers, the method comprising:
contacting glycerol and tertiary butanol (TBA) in the presence of an acidic catalyst to produce one or more glycerol ethers selected from mono-tert butyl glycerol ethers, di-tert butyl glycerol ethers, tri-tert butyl glyc- erol ethers, or a combination thereof, wherein the contacting is performed in the presence of hydrogen;

separating water and a stream comprising isobutylene, unreacted TBA, or a combination thereof from the one or more glycerol ethers; and recycling at least a portion of the stream comprising isobutylene, unreacted TBA, or a combination thereof to the contacting.

2. The method of claim 1, wherein the molar ratio of TBA to glycerol is in the range of from 2:1 to 7:1.

3. The method of claim 1, wherein the separating comprises separating an overhead comprising isobutylene, unreacted TBA, water, or a combination thereof from a bottoms stream comprising the one or more glycerol ethers, and separating water from the overhead to provide the stream comprising isobutylene, unreacted TBA, or a combination thereof.

4. The method of claim 1, wherein the contacting is performed in a reactive distillation column.

5. The method of claim 1 further comprising separating di-tert butyl glycerol ethers, tri-tert butyl glycerol ethers, or a combination thereof from the one or more glycerol ethers.

6. A method comprising:

introducing glycerol and tertiary butanol (TBA) into a reactor comprising an acidic catalyst to produce one or more glycerol ethers selected from mono-tert butyl glycerol ethers, di-tert butyl glycerol ethers, tri-tert butyl glycerol ethers, or a combination thereof, wherein the introducing step is performed in the presence of hydrogen, and wherein the reactor is operated at a molar ratio of TBA to glycerol in the range of from 2:1 to 7:1.

7. The method of claim 6 further comprising separating water and a stream comprising isobutylene, unreacted TBA, or a combination thereof from the one or more glycerol ethers; recycling at least a portion of the stream comprising isobutylene, unreacted TBA, or a combination thereof to the contacting; or both.

8. The method of claim 6 further comprising separating one or more di-tert butyl ethers, tri-tert butyl ethers, or a combination thereof from the one or more glycerol ethers.

9. The method of claim 6, wherein the acidic catalyst has a Hammett acidity function $H_o$ in the range of from −12 to −16.

10. The method of claim 6, wherein the acidic catalyst comprises an acidic ion exchange catalyst, and wherein the acidic ion exchange catalyst comprises sulfonic acid groups, is macroreticular, comprises a polymeric resin, or a combination thereof.

11. The method of claim 6, wherein the reactor further contains an oligomerization catalyst effective to catalyze the oligomerization of isobutylene to provide one or more branched olefins.

12. The method of claim 11 further comprising separating one or more of the one or more branched olefins from the one or more glycerol ethers for use as a gasoline fuel additive or a precursor therefor.

13. The method of claim 6, wherein an overall selectivity to glycerol ethers (defined as carbon selectivity) is at least 15 percent (%), wherein a glycerol conversion (defined as the moles of glycerol converted divided by the moles of glycerol fed) is at least 70%, wherein a TBA conversion (defined as the moles of TBA converted divided by the moles of TBA fed) is at least 55%, or a combination thereof.

14. A method of producing at least one fuel additive, the method comprising:

introducing glycerol and tertiary butanol (TBA) into a reactor comprising an acidic catalyst effective to catalyze the reaction of glycerol and isobutylene to produce one or more glycerol ethers selected from mono-tert butyl glycerol ethers, di-tert butyl glycerol ethers, tri-tert butyl glycerol ethers, or combinations thereof, and an oligomerization catalyst effective to catalyze the oligomerization of isobutylene and thus provide one or more branched olefins including diisobutylene, wherein the introducing is performed at a molar ratio of TBA to glycerol in the range of from 2:1 to 7:1, and wherein the introducing is performed in the presence of hydrogen;

separating the branched olefins, isobutylene, or both from the one or more glycerol ethers;

hydrogenating at least a portion of the branched olefins to produce isooctane; and combining at least a portion of the one or more glycerol ethers with a diesel fuel, combining at least a portion of the isooctane with a gasoline fuel, or a combination thereof.

15. The method of claim 14, wherein the acidic catalyst has a Hammett acidity function $H_o$ in the range of from −12 to −16; wherein the oligomerization catalyst comprises a medium pore zeolite having a structure comprising ten tetrahedra in a ring; or a combination thereof.

16. The method of claim 14, wherein the acidic catalyst:

comprises an acidic ion exchange catalyst, wherein the acidic ion exchange catalyst comprises sulfonic acid groups, is macroreticular, comprises a polymeric resin, or a combination thereof; or comprises a keggin-type polyoxometalate supported on alumina, silica, zirconia, MCM-41, SBA-15 or a combination thereof.

17. The method of claim 14, wherein an overall selectivity to glycerol ethers (defined as carbon selectivity) is at least 15 percent (%), wherein a glycerol conversion (defined as the moles of glycerol converted divided by the moles of glycerol fed) is at least 70%, wherein a TBA conversion (defined as the moles of TBA converted divided by the moles of TBA fed) is at least 55%, wherein an overall olefin selectivity (defined as selectivity towards C2-C12 olefins on a carbon basis) is at least 40%, wherein a selectivity to diisobutylene (defined as selectivity towards diisobutylene on a carbon basis) is at least 35%.

* * * * *